(12) United States Patent
Bondurant

(10) Patent No.: US 7,046,356 B2
(45) Date of Patent: May 16, 2006

(54) METHOD FOR PROCESSING IN SITU INSPECTION REFORMER TUBE DATA

(75) Inventor: Phillip D. Bondurant, Kent, WA (US)

(73) Assignee: Quest TruTec, LP, La Porte, TX (US)

( * ) Notice: Subject to any disclaimer, the term of this patent is extended or adjusted under 35 U.S.C. 154(b) by 26 days.

(21) Appl. No.: 10/707,629

(22) Filed: Dec. 25, 2003

(65) Prior Publication Data

US 2004/0114793 A1 Jun. 17, 2004

Related U.S. Application Data

(62) Division of application No. 09/713,415, filed on Nov. 15, 2000.

(51) Int. Cl.
*G01N 21/00* (2006.01)

(52) U.S. Cl. ..................... 356/241.1; 382/141
(58) Field of Classification Search ... 356/237.1–237.6, 356/241.1–241.2; 382/141
See application file for complete search history.

(56) References Cited

U.S. PATENT DOCUMENTS

| | | | | |
|---|---|---|---|---|
| 3,602,596 A | * | 8/1971 | Astheimer et al. | 356/51 |
| 4,199,258 A | * | 4/1980 | Dau | 356/626 |
| 4,305,561 A | * | 12/1981 | Hunter et al. | 248/228.3 |
| 4,440,496 A | * | 4/1984 | Milana | 356/241.1 |
| 4,465,374 A | * | 8/1984 | Pryor et al. | 356/635 |
| 4,861,984 A | * | 8/1989 | West | 250/236 |
| 4,967,092 A | * | 10/1990 | Fraignier et al. | 250/559.07 |
| 5,099,115 A | * | 3/1992 | Cruickshank | 250/236 |
| 5,933,231 A | * | 8/1999 | Bieman et al. | 356/241.1 |
| 6,462,815 B1 | * | 10/2002 | Drabarek et al. | 356/241.1 |

FOREIGN PATENT DOCUMENTS

JP 403075544 A * 3/1991

* cited by examiner

*Primary Examiner*—Hoa Q. Pham
(74) *Attorney, Agent, or Firm*—Hayward A. Verdun

(57) ABSTRACT

The present invention relates to a method for processing a signal obtain, from an in situ reformer tube inspection, that includes X, Y, and intensity data sets for each pixel of a sensor from an image sensor receiving a substantially ring shaped image. The method converts a signal having an X position, a Y position, and an intensity component to a signal having an angle, a radius, and an intensity and filtering out all signal sets that do not have a radius greater than a predetermined radius.

9 Claims, 5 Drawing Sheets

METHOD FOR PROCESSING IN SITU INSPECTION REFORMER TUBE DATA

CROSS REFERENCE TO RELATED APPLICATIONS

This application is a divisional of and claims the benefit of U.S. Non-Provisional Application Ser. No. 09/713,415 filed Nov. 15, 2000 under 35 U.S.C.§120.

The present patent application is related to our co-pending application entitled "A Method For Reformer Tube In Situ Inspection Radius Calculation," U.S. application Ser. No. 10/707,630 filed Dec. 25, 2003, which is incorporated by reference as if fully set forth herein.

BACKGROUND OF INVENTION

1. Field of the Invention

The present invention relates to inspection of materials, and more particularly to the inspection of the surface of materials for creep, metal dusting, irregularities, and manufacturing flaws. With still greater particularity the invention pertains to the inspection of the interior of cylindrical surfaces such as reformer tubes used in chemical processing.

2. Description of the Related Art

Reformer tubes are used in many chemical processes. Examples include tubes used to produce ammonia, methanol, hydrogen, nitric and sulfuric acids, and cracking of petroleum. Reformer tubes, also called catalyst tubes, are one of the highest cost components of such plants both in capital and maintenance. A typical installation consists of several hundred vertical tubes. These tubes represent a significant cost for replacement and can be a major source of plant unavailability if unplanned failures occur.

Such tubes are frequently subjected to pressure changes and contact with corrosive substances. Under such situations creep, metal dusting, and surface irregularities frequently develop. If left untreated, creep will develop into cracks that will propagate leading to failure of the tube.

The plant operator is faced with balancing production needs against tube life and risk of tube failure. The Inner Diameter (ID) of these reformer tubes is generally between 76 mm (3.0 inches) and 127 mm (5.0 inches). During plant operation the catalyst filled tubes are externally heated to allow the reforming reaction to occur. One of the major concerns in plant operation is that the reformer tubes operate at an elevated temperature such that they are susceptible to a failure mechanism referred to as "creep". This condition exists due to the elevated temperatures and stresses imposed by internal pressure, thermal gradients, and mechanical loading cycles. Being able to identify and locate such damage in its early stages is essential for optimizing plant operation.

Conventional Nondestructive Examination (NDE) inspection techniques currently applied to reformer tubes are geared to finding creep damage in the form of internal cracking. However, with the trend towards larger tube diameters and longer intervals between turnarounds, the detection of such defects may not allow for sufficient time for forward planning of tube replacements. Also, such "end of life" techniques do not allow any differentiation between the "good" tubes. Early detection of underutilized tube life can prevent the lost opportunity on both unrealized production through running them too cool and tube life "giveaway" if good tubes are discarded prematurely.

Typically, destructive testing is used on a small number of tubes removed from the reformer to try and determine the absolute life remaining. Whatever the method is used, the results are used on a sample size that is not statistically valid. It is preferable that all the tubes be surveyed with a NDE technique to characterize their relative condition in order to make sense of the absolute condition assessment provided by the destructive testing.

Reformer tubes undergo creep strain, in the form of diametrical growth, on the first day that they are fired. The ability to accurately measure and record this growth means that the tubes' condition can be monitored on day one. Therefore, not only can individual tubes be retired from service at an appropriate time, but also the reformer as a whole can be assessed for performance.

Another problem that can occur in reformer tubes is metal dusting. Metal dusting is a condition where the process stream attacks the interior of the reformer tube with subsequent, significant metal loss. This can be severe enough to be the life limiting condition for the tube. Typically, the metal dusting damage is limited to a 360° circumferential band around the catalyst tube's interior surface where the critical temperature range exists.

External diameter measurements have been used but they are limited as the automated devices only measure across one diameter and are often access-restricted by tube bowing. Manual measurements are too time consuming to provide more than a few readings per tube. No external measurement method can provide diameter growth data at or through the reformer refractory. External measurements are inherently less precise as they are based on a cast surface rather than the internal machined surface and do not take into account the effects of oxide shedding. The most accurate growth measurements are obtained when 'as new' baseline data has been taken prior to the tube being fired for the first time. However, if this is not available by using the top portion of the tube that is operating outside the creep temperature as a reference diameter, the growth profile of the tube can be determined at any stage in its life.

Accordingly, there is a need for an automated method and apparatus capable of examining the internal surfaces of reformer tubes. The method should be nondestructive and provide both absolute and relative information on tube profile.

SUMMARY OF INVENTION

The present invention has been made in view of the above circumstances and has as an aspect a method for inspecting a reformer tube for chemical processing for damage such as creep and metal dusting. The method includes the steps of focusing a coherent light beam onto an interior of a tube or piping and detecting at least a portion of a reflection of the light beam from the tubing by converting the detected light beam into an electrical signal and the processing of the electrical signal to determine a radius of tube under-going in situ inspection.

An embodiment of the invention employs a solid-state laser diode. A focusing lens is located in front of the diode to focus the laser at a spot on the surface of the tube to be inspected. The diode and focusing lens are rotatable within the tube to allow the spot to form a ring as they are rotated. As the probe moves through the tube the spot scans the entire surface. A photo detector is arranged behind an imaging lens to detect the intensity of the spot. Both the detector and the imaging lens rotate in the same fashion as the laser diode and its focusing lens. The optical paths are selected so that the diode, photo detector and surface of the tube form a triangle. The distance between the detector and diode is fixed. This results in the reflected spot moving on the surface of the photo detector in proportion to the distance to the internal surface of the tube. Signal processing means can then use that information to reconstruct a three dimensional image of the internal surface of the tube. The image may either be displayed on a monitor or printed for later review.

With present technology a 15-meter tube can be inspected within three minutes. An inspection such as this will provide over 1,000,000 radius readings. The method provides means to compress this information to allow easy manipulation and analysis.

A further aspect of the present invention employs a laser or light emitting diode (LED) and a cone shaped reflector to project a ring of illumination on the interior of the tube to be inspected. A charge-coupled device (CCD) is arrayed so as to scan the ring and report the reflectivity and profile. Signal processing circuitry reconstructs an image of the interior of the tube.

The use of the internal laser mapping technique is not only useful in preventing tube failure but has huge potential in optimizing production from the whole tube set without sacrificing reliability.

Additional aspects and advantages of the invention will be set forth in part in the description which follows, and in part will be obvious from the description, or may be learned by practice of the invention. The aspects and advantages of the invention will be realized and attained by means of the elements and combinations particularly pointed out in the appended claims.

To achieve these and other advantages and in accordance with the purpose of the present invention, as embodied and broadly described, the present invention can be characterized according to one aspect of the invention as comprising a method for the in situ inspection of a reformer tube or similar type tube or piping used in chemical processing for damage such as creep and metal dusting. The method includes the steps of focusing a coherent light beam onto an interior of the tube and detecting at least a portion of a reflected light beam and converts the detected light beam into an electrical signal and further processes the electrical signal to determine a radius of the tube.

It is to be understood that both the foregoing general description and the following detailed description are exemplary and explanatory only are not restrictive of the invention, as claimed.

BRIEF DESCRIPTION OF DRAWINGS

The accompanying drawings, which are incorporated in and constitute a part of this specification, illustrate several embodiments of the invention and together with the description, serve to explain the principles of the invention.

DETAILED DESCRIPTION

Reference will now be made in detail to the present embodiments of the invention, examples of which are illustrated in the accompanying drawings. Wherever possible, the same reference numbers will be used throughout the drawings to refer to the same or like parts (elements).

Figure 1:
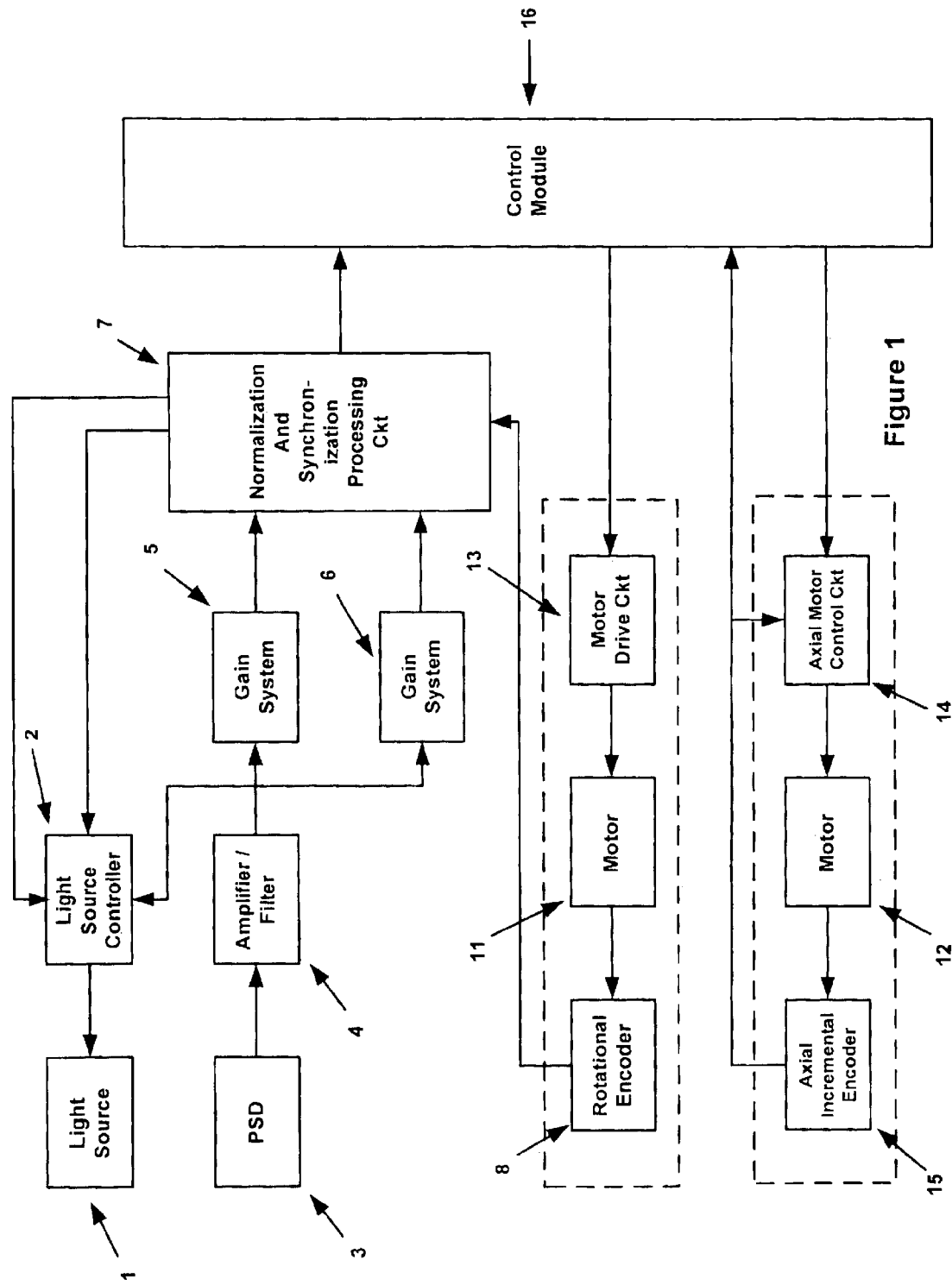
FIG. 1 is a block diagram of an embodiment of the Invention.

FIG. 1 is a block diagram of an embodiment of the invention. Components may be either hardware components or software modules as described below. The probe includes a light source 1.

The purpose of the light source 1 is to project a spot of light on the surface (not shown) to be inspected. Light source 1 is typically a laser diode or light emitting diode (LED). A light source controller 2 is connected to light source 1. Controller 2 sets and controls the optical power level of light source 1. The power level may either be fixed or varied to produce a preset signal level.

A position sensitive photo detector (PSD) 3 is situated so as to detect the spot made by light source 1. Photo detector 3 may be a lateral effect photodiode, photodiode array, or charge coupled device (CCD). This description assumes the device chosen for 3 is a lateral effect photodiode. Detector 3 may have either one or two axes, dependant upon the specific measurement geometry. In this description only a single axis detector and associated lens (not shown) is used. Similarly a 2D detector may be used for 3 if the light beam from light source 1 is rotated, by means of a rotating mirror, and detector 3 is fixed. An amplifier filter 4 is connected to detector 3. Amplifier/filter 4 converts the small signal currents generated by detector 3 into voltages. A filter sets the bandwidth of the system.

The required bandwidth is determined by a combination of the speed of probe spin and the required sample rate. Amplifier and filter may be combined into a single unit by inserting active components into a differential amplifier to produce an active filter. A suitable amplifier may be an integrated circuit differential amplifier such as a AD712. A feedback path is provided between amplifier/filter 4 and light source controller 2 to allow control of light source 1 dependant upon the intensity of signal received at detector 3. One or more gain systems 6 may be connected to the output of amplifier/filter 4.

This embodiment shows 2 gain systems (5 and 6) each providing a different level of gain. The addition of one or more additional gain systems increases the dynamic range of the system and allows rapid changes of surface reflectivity to be measured. The outputs of the several gain stages are recorded simultaneously, and the largest value that is below saturation is used. Several gain systems may be connected in parallel to provide usable signals in all situations.

A normalization and synchronization processing circuit 7 is connected to the output of gain system 6. The first function of system 7 is to select the signal from multiple gain systems 6 with the maximum dynamic range without saturation. The second function is to convert the individual detector readings to a calibrated measurement of the distance between light source 1 and the surface to be scanned. For a 1 D detector the calibration may be found by solving equation 1 as the follows:

$$\text{Measurement} = g \cdot \frac{v_1 - v_2}{v_1 + v_2} \qquad \text{EQ. 1}$$

In the equation 1, $v_1$ and $v_2$ are the current readings from either end of detector 3. (g) is a calibration function used to remove non-linearity in the detector and optics. (g) may be determined empirically by scanning calibrated tube samples of various diameters and using the resultant data points to find coefficients of the function (g). As an alternative to the calculation using (g) in the above equation, a lookup table with some form of interpolation may be used. In order to eliminate electronic drift the system periodically turns light source 1 off and measures electronic offset voltages. The offset voltages are then subtracted from subsequent readings made with light source 1 on. Normalization and synchronization processing circuit 8 also measures the surface reflectivity. The reflectivity of the surface is computed from the detector signal level, gain, and light source power level. Variations in surface reflectivity can provide useful information about the surface. Normalization and synchronization processing circuit 7 also collects data from a rotational encoder in 8. The correlation of the signals from encoder in 8 and from photo detector 3 assures equally spaced samples around the circumference of a tube.

Two motors 11 and 12 move the probe. The first motor 11 rotates the probe within a tube. A motor drive circuit 13 controls motor 11. Encoder 8 is connected to motor 11 allowing determination of the absolute rotational position of the probe. The output of encoder 8 is connected to normalization and synchronization processing circuit 7. A second motor 12 provide axial positioning of the probe. A second motor drive circuit 14 controls motor 12. An axial incremental encoder 15 connected to motor 12 provides information on the axial position of the probe in the tube.

A system data storage display and control module 16 provides overall control of the probe. Module 16 receives information on the distance between light source 1 and the surface sought to be inspected and surface reflectivity from normalization and synchronization processing circuit 7. Module 16 also receives information about the axial position of the probe from encoder 15. Module 16 controls the rotational position of the probe in the tube by sending an on and off signal to rotational motor drive circuit 13. Module 16 also controls the axial position by sending on/off and forward/backward signals to axial motor control circuit 14.

Figure 2:
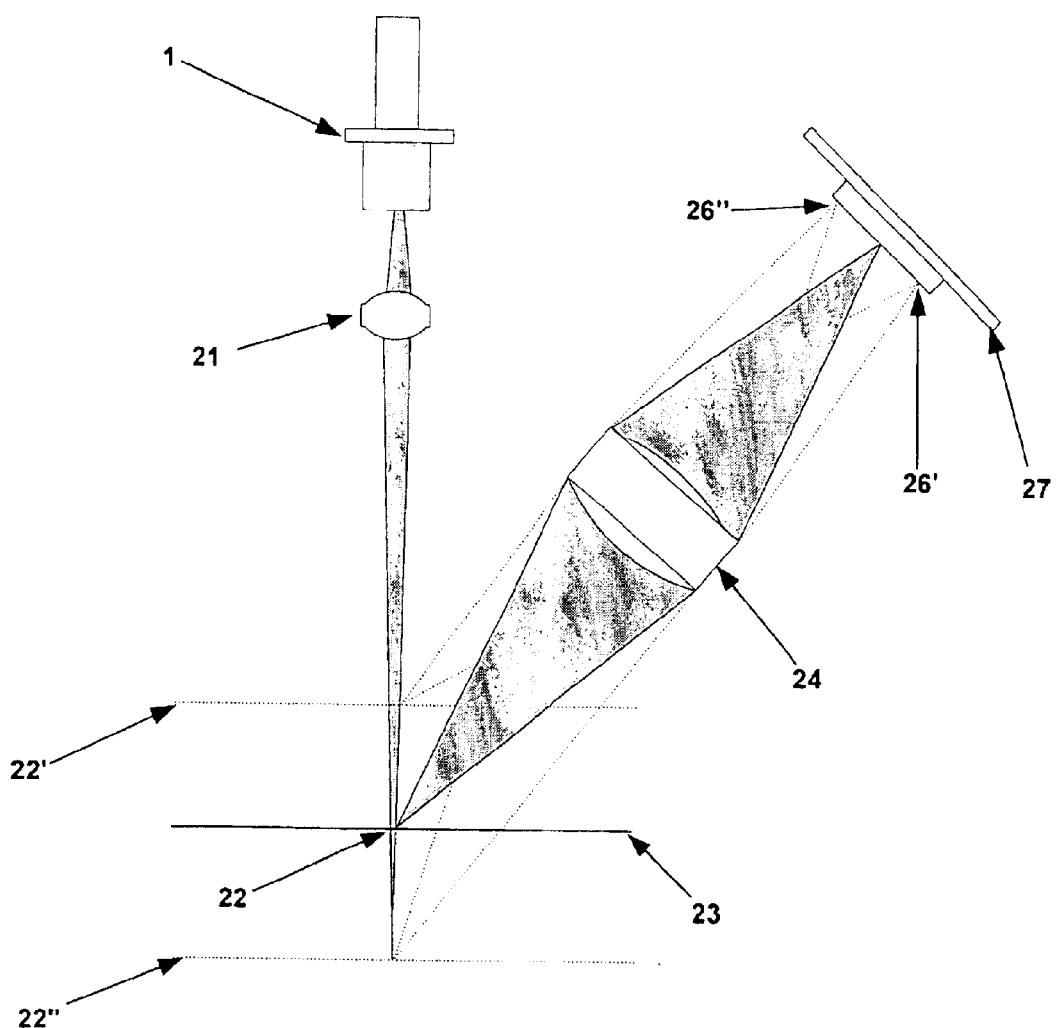
FIG. 2 is diagram of the optical components of the FIG. 1 embodiment.

FIG. 2 is diagram of the optical components of the FIG. 1 embodiment. A light source 1 produces beam of light. Light source 1 is usually a diode laser but could be a light emitting diode in special applications. A collimating lens 21 downstream of light source 1 converts the light emitted by light source 1 into a collimated beam which does not spread to any appreciable extent over the inspection range 22"—22".

The beam produces a target spot 22 where it impacts the target surface 23. A photo detector 27 is mounted at an angle to the optical train of components 1, 21, and 22. The angle is detected such that the imaged spot at 26 is in focus over the measurement range 22" to 22". Photo detector 27 is usually a lateral effect photodiode array or charge coupled device (CCD) photo detector. Photo detector 27 may either be a one dimensional (1D) or two dimensional (2D) device. If photo detector 27 is a 2D device additional information may be generated at the expense of greater bandwidth. An imaging lens 24 is mounted in front of photo detector 27. Imaging lens 24 projects an image of the surface of target 23 onto photo detector 27. The image projected onto photo detector 27 includes an image 26 of the spot 22 where the collimated beam impacts the target. The position of imaged spot 26 varies with the distance from light source 1 to target 23 due to parallax. If, for example, the surface of target 23 is at 22" the imaged spot is at 26". Similarly, if the target is at 22" the imaged spot will be at 26". The result is that imaged spot 26 moves back and forth across the surface of photo detector 27 in an amount relative to the distance between target surface 23 and light source 1. Photo detector 27 thus generates an electrical signal containing information about the distance between 1 and 23.

The complete optical system, as described, is rotated around the central axis of the probe in order to scan the complete circumference of the tube. Other embodiments modify the basic optical system to reduce the need for slip rings for the electrical signals required by the laser diode and detector. By locating the laser diode source and collimating lens on axis with the probe longitudinal axis and using a rotating 45° mirror to deflect the light beam at a right angle to the probe longitudinal axis, the beam can be made to scan the circumference of the tube. A second mirror and imaging lenses are also rotated with the first mirror, to form an image of the light spot onto a stationary 2D PSD. This approach has the advantage of eliminating slip rings from the probe. The disadvantage is that the 2D PSD provides 4 outputs instead of 2, and requires more processing to compute the radius data.

Another disadvantage of this method is that a transparent tube or windows in the housing are required to support the laser diode and detector, while still allowing a light path. The window or transparent tube are subject to scratches or dirt which provide reflection paths for light leakage between the laser diode source and the detector. These light leakage paths cause errors in the radius measurement. Also, the electrical wires necessary to connect to either the diode or detector must cross the path of the light beam at some point in the rotation of the lens/mirror assembly. Other variations of the optical arrangement are possible. The embodiments described herein are not intended to limit the scope of the invention, but rather are for illustrative purposes.

Figure 3:
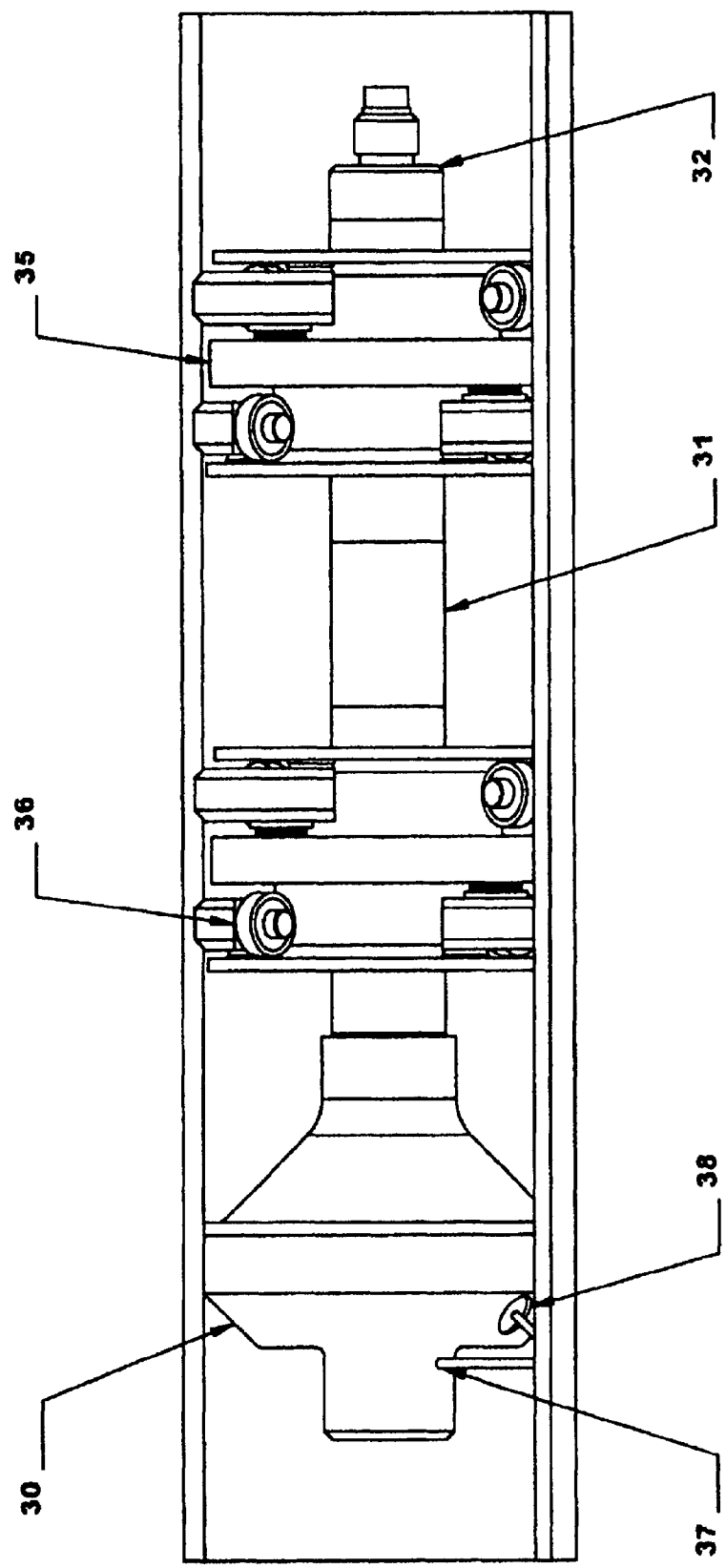
FIG. 3 is a perspective detail view of the probe of the invention.

FIG. 3 shows a detailed profile view of the probe of an embodiment in this invention. The probe consists of a rotating optical head 30 mounted to a body 31. The relative size of the reformer tubes present other challenges to laser-optical probe design. Previous probes of this type have been for smaller diameter tubing, up to 2-inches in diameter. For larger diameter tubes, such as reformer tubes, the weight and inertia of the probe and its rotating components must be reduced to make the approach practical. In one embodiment of the system, the probe head 30 is spinning at 1800 rpm. Replacing a metal spinning head with one made of Delrin™, an engineering plastic made by Dupont, provides weight and inertia reduction while maintaining structural strength, thermal stability, and impact resistance.

The probe body 31 is made relatively small compared to the diameter of the reformer tube. This allows weight reduction, and has the benefit of allowing the same probe body to be used in several different tube sizes by changing the centering spring assemblies, and the probe head. Weight reduction is important in the reformer tube application because the probe is drawn through the tube by a motorized positioning system. Reducing the weight reduces the size and cost of the positioning system.

A tether and electrical connections are made to the probe through connector 32. Electrical connections between the connector and the optical head are made through the probe body by means of an internal slip-ring. Probe rotation is by means of a motor inside probe body 31. Centering rings 35 are spring loaded arms with non-metallic wheels to hold the probe in the center of the tube, and allow for axial motion through the tube.

Reformer tubes are made of special alloys to withstand the temperature and pressure regimes to which they are subjected. During normal operation, portions of reformer tubes operate at or near the structural stability limit of the tube metallurgy. If the probe leaves any traces of other metals on the inner tube surfaces, such as aluminum or lead, the traces of these metals will enter the pores of the tube wall and cause rapid cracking and failure of the tube. Therefore, it is important that only non-metallic components be used where the probe is in contact with the tube surface. The probe's centering spring mechanism 35 contacts the sides of the tube with wheels 36 made from Delrin™, an engineering plastic with metal-like properties.

One of the problems that affects accuracy in PSD based laser triangulation systems is when unintended reflections cause additional light to impinge on the sensor. These reflections arise when light reflects from the surface being measured, bounces off other surfaces and enters the detector from various angles. Because the PSD sensor measures the centroid of the light imaged on its surface, reflections cause a skewing of the image centroid. The present invention minimizes reflections by placing the laser 37 at the front of the probe head and in front of the detector 38. In contrast to designs with the laser behind the detector, this reduces the exposure of the detector to light reflections off the probe head 30, body 31, and centering spring assemblies 35.

Figure 4:
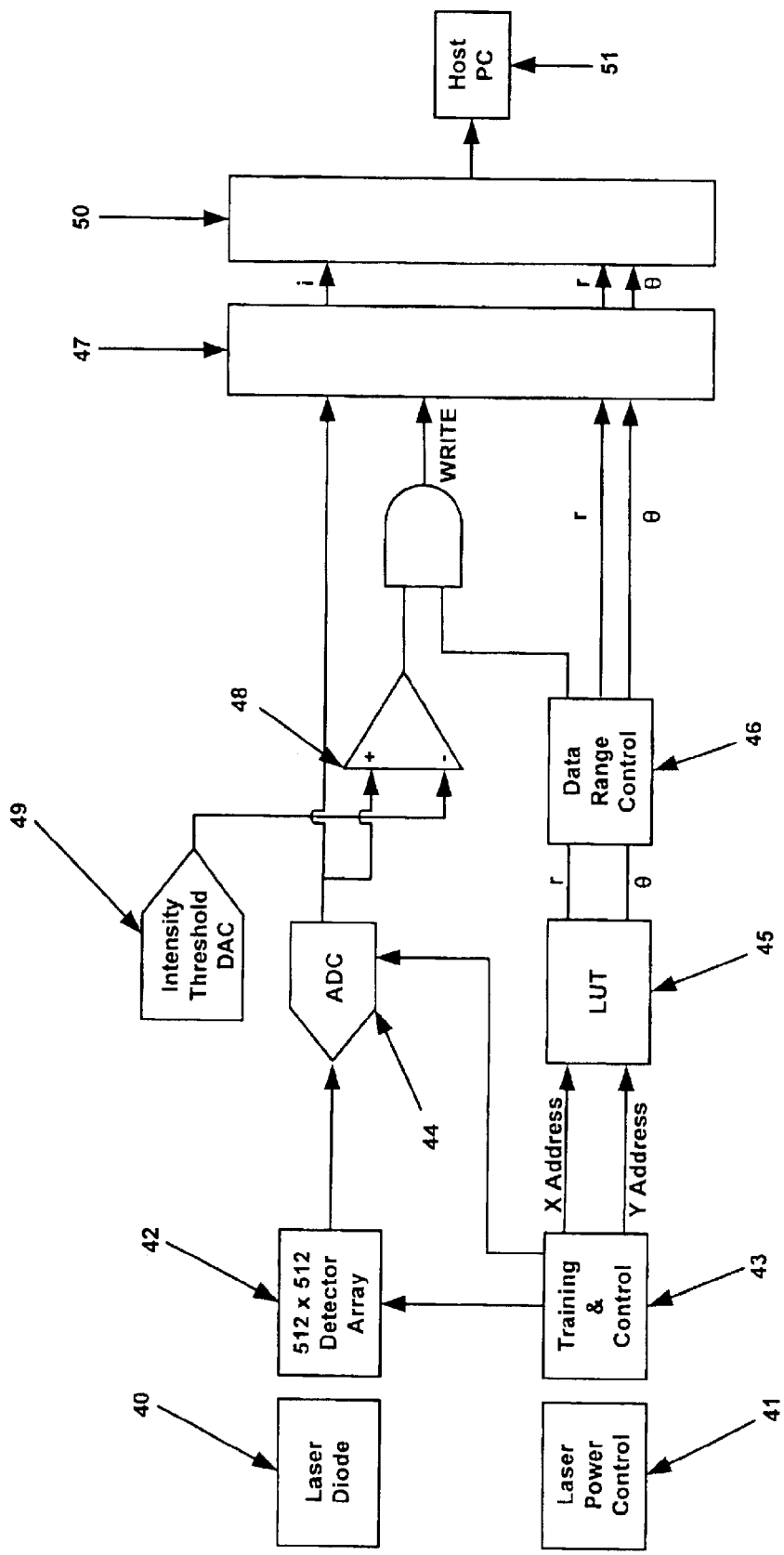
FIG. 4 is a block diagram of an alternate embodiment of the Invention.

FIG. 4 is a block diagram of an alternate embodiment of the invention. This embodiment projects a ring of light onto the interior surface of the reformer tube. The ring is then scanned with an array of light sensors to produce and reconstruct an image of the interior of the tube.

A light source 40 is connected to a power controller to maintain a light level sufficient to be sensed by an image detector. Typically light source 41 is a laser diode with output in the infrared or visible portion of the spectrum. A light detector 42 is positioned in such a manner as to view an image of the ring of light. Light detector 42 is a two dimensional array of photosensitive cells. Most commonly detector 42 is a Charge Coupled Device (CCD) array of photocells. Such arrays are commonly used in video cameras. Array 42 is divided into individual pixels each represented by an X coordinate and a Y coordinate. The signal from each pixel is proportional to the intensity of light falling on that pixel. The detector is controlled by a timing and control module 43. In general, module 43 scans the array in a line-by-line fashion. Each individual line is moved to an output register. The individual pixels are then shifted out in a serial operation. The CCD array is of the Frame Transfer type which uses two identical CCD arrays, one for scanning and one for storage. The second array is shielded from light and acts a buffer to allow reading an image while a second image is being formed on the first array. A typical sensor is a 512×512 array having 262,144 elements or pixels. Typically, there are additional light shielded pixels in the array which provide buffering of the active pixels. This increases the number of total pixels which must be read.

A typical 512×512 array requires a clock speed of 80 Mhz to read out with time for the buffer pixels, transferring the frame, etc., for a 120 Hz frame rate. Some arrays have a split output structure, so that two pixels are read at a time. This reduces the clock rate to 40 Mhz, but requires two parallel output processing channels. In tested prototypes the ring image has a thickness of 3–5 pixels. At the maximum radius the number of pixels actually used is provided by equation 2 as follows:

$$2 \cdot \pi \cdot r \cdot 5 \cong 8k \text{ pixels} \qquad \text{EQ. 2}$$

Where r, at the maximum radius is 256 for a 512×512 array. In other words each frame will hold about 8 k pixels of useful information.

During use, array 42 converts the image to an array of intensity values. The Analog to Digital Converter 44 connected to Array 42 converts this analog signal to a digital one. An eight-bit A to D converter has been found suitable for 44. The signal next goes to a Look-Up-Table (LUT) 45 to convert the Cartesian X, Y coordinates received from the Timing and Control Module 45 into radial coordinates r, $_r$. LUT 45 may be a logical array or an addressable device such that when an X, and Y address is input, a value for r and φ is provided. This may be done with non-volatile memory devices such as ROM, PROM, EPROM, EEPROM, flash memory, or a volatile memory such as static or dynamic RAM. The speed of operation required for this embodiment dictates the use of volatile memory, such as synchronous RAM. The access time must be under 30 nanoseconds for a 512×512 array. A 256 k×18 device provides 9 bits each for r and φ. For a 10-bit φ, the MSB of the Y address value can be added to φ to form 10 bits. A 9-bit φ is used for 360 points per rotation, 10 bits for 720 points per rotation, for ½° resolution.

The X and Y address of each pixel is fed to the address lines of the LUT at the same time that the value of intensity for the pixel is available from the A to D converter 44. Because LUT 45 is a volatile memory device, it must be loaded with the lookup values before use. This may be done on power up of DSP 50 or host PC 51. LUT 45 is programmed with the corresponding r and φ for each X and Y address of sensor 42 according to equation 3 as follows:

$$r = SQRT(X^2 + Y^2), \phi = \tan^{-1}(Y/X) \qquad \text{EQ. 3}$$

The intensity value from array 42 and the r, φ values from LUT 45 are sent to a Data Range Control module (DRC) 46. DRC 46 reduces the amount of data used in further processing steps. The actual image from array 42 includes only about 8 k of pixels out of a typical 256 k pixels in a 512×512 array. The pixels of interest are in a circular area in the outer third of the array. The definition of the pixels of interest t is $r > r_t$ where $r_t$ is the radius threshold value and is the minimum r value of interest. No image data ever occurs at r-values less than $r_t$. DRC 46 includes logic circuitry which only passes to FIFO 47 the information of interest i.e. $r > r_t$.

Even with the use of DAC 47 there are still too many pixels without useful information for easy processing. For example in a 3-in ID pipe with a probe measuring range from 2.25 in to 2.75 in. radius and a 512×512 array the measuring range will cover 85 pixels with r having a range of from 171 to 256. If $r_t$ is set to 170 there are still over 170,000 pixels per frame to be processed. Only the pixels that are illuminated by the light source 40 provide useful information. Since only pixels with intensity over a certain threshold are of interest that fact may be used to eliminate surplus pixels. A high-speed comparator 48 is used to compare the intensity value of each pixel with a threshold value $I_t$. The output of comparator 48 triggers the data selection to pass only the data including r, φ, and I, where I is greater than the threshold $I_t$. This reduces the data sent to FIFO to about 8 k pixels. The threshold value $I_t$ is set with a DAC device 49. DAC 49 is set from the host system via the DSP controller 50 during calibration.

Since the actual data rate is greater than 40 MHz accordingly; a FIFO 47 is used to buffer the data at that rate. Data entering FIFO 47 clocks at the scan rate of the array 42 but is sporadic and has many gaps due to the action of the data selection effect of DRC 46 and comparator 48. FIFO 47 buffers the data for DSP 50, which is thus able to read the data at a slower rate. DSP 50 must still process all 8 k of data in under 8.3 milliseconds in order to process 120 frames/sec. FIFO 47 will buffer one frame of data for an 8 k FIFO or two frames for a 16 k FIFO.

The Digital Signal Processor (DSP) 50 performs the actual computation of the radius of the tube by finding the centroid of the imaged light on each radial spoke $\phi_k$ where k indexes the angle through 360 or 720 increments depending on the resolution. The centroid for each radial spoke $\phi_k$ is computed according to equation 4 as follows:

$$\frac{\sum_i r_i \cdot I_i}{\sum_i I_i} \qquad \text{EQ. 4}$$

Where r is the radius value from 0 to 255 for a 512×512 array, and I is the corresponding intensity value for that pixel, i is the index value for the array of points comprising the radial spoke. In practice, i starts at a radius much larger than 0 since the image is set in the outer third of array 42. A DSP 50 of sufficient speed can perform the division and provide the radius value directly. If a lower speed DSP 50 is used it can compute the numerator and denominator of the above equation and provide the values as separate outputs. A post processing operation in host PC 51 computes the actual radius value and converts the output to engineering units such as inches or millimeters. The processed data is sent to host PC 51 via a high-speed interface; suitable methods include serial interfaces such as RS232, RS485, USB, or IEEE-1394 (Firewire) or parallel interfaces such as a PC parallel port or EPP.

Host PC 51 receives the data from the probe processing system, and does any post processing of the data and formats it for storage on hard disk or removable media storage and displays the data on a graphics screen.

FIG. 4 illustrates an implementation having a single processing channel. For an image sensor with a dual output structure, another channel of processing is added with another A/D converter, LUT, Data Range Controller, comparator, and FIFO.

Figure 5:
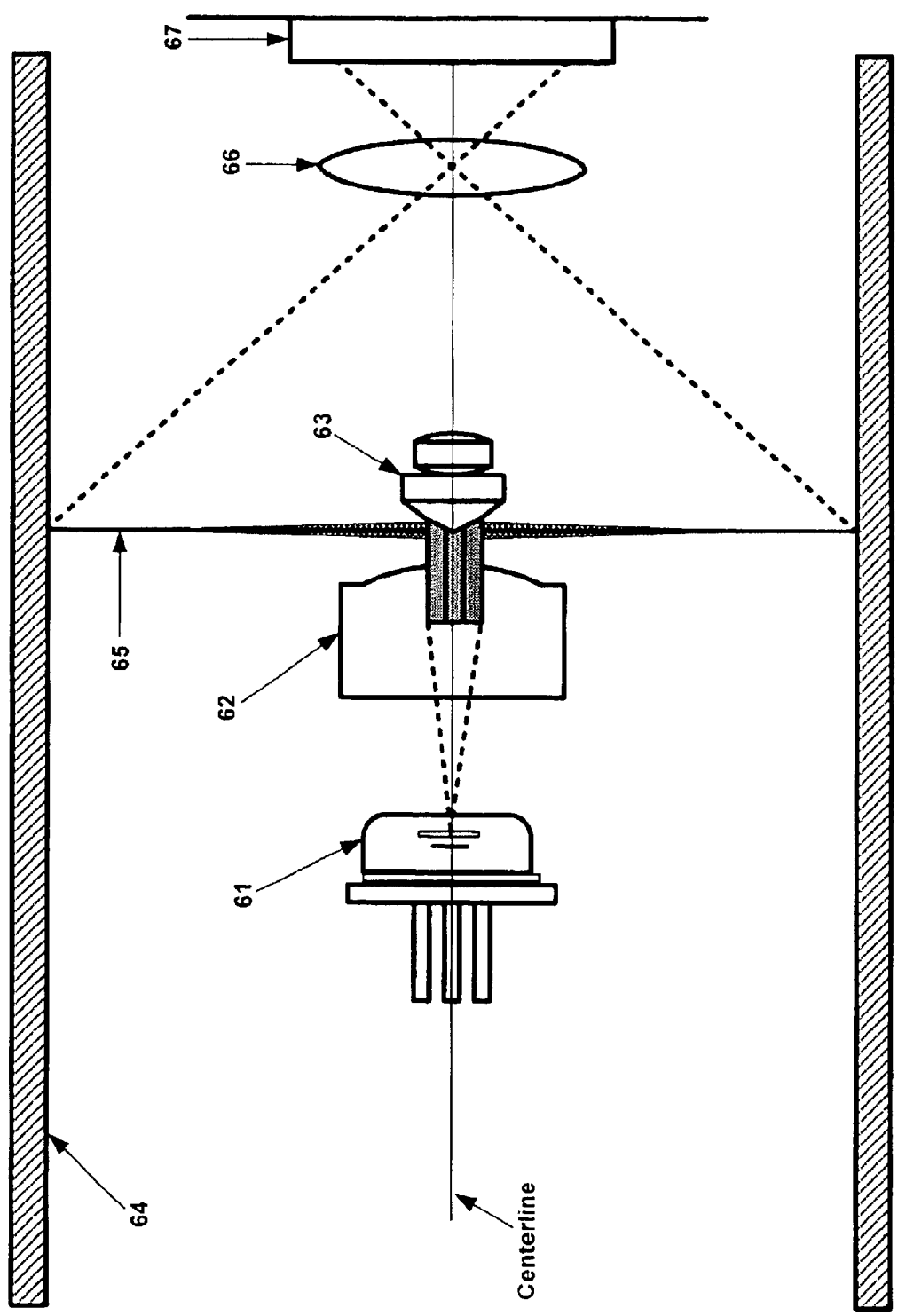
FIG. 5 is diagram of the optical components of the FIG. 4 embodiment.

FIG. 5 is a front elevation view of the optical system of the FIG. 4 embodiment. The components are located in a tube 64 to be inspected. A laser diode 61 is located at the center of tube 64 in such a manner that the light emitted by diode 61 is parallel to the axis of tube 64. A collimation lens 62 is located on said axes to focus the light on the interior surface of tube 64. A cone mirror 63 is located coaxial to diode 61 and lens 62 to form the light emitted from diode 61 and collimated by lens 62 into a ring 65 on the surface of tube 64. Mirror 63 is preferably a parabolic conical mirror to aid in focusing the beam on the interior surface of the tube. An imaging lens 66 coaxial with diode 61 lens 63 and mirror 63 is situated in such a manner as to project an image of ring 65 onto the surface of an imagining array 67. Imaging array 67 senses the image projected onto its surface and converts the image into electrical signals.

The above examples and embodiments are exemplary only the invention being defined solely by the attached claims.

It will be apparent to those skilled in the ar, that various modifications and variations can be made in the "A Method For Reformer Tube In Situ Inspection Radius Calculation" of the present invention and in construction of this invention without departing from the scope or intent of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Reference will now be made in detail to the present embodiments of the invention, examples of which are illustrated in the accompanying drawings. Wherever possible, the same reference numbers will be used throughout the drawings to refer to the same or like parts (elements).

What is claimed is:

1. A method for processing a signal that includes X, Y, and intensity data sets for each pixel of said sensor from an image sensor receiving a substantially ring shaped image comprising the steps of, converting a signal having an X position, a Y position, and an intensity component to a signal having an angle, a radius, and an intensity and filtering out all signal sets that do not have a radius greater than a predetermined radius.

2. A method for processing a signal as in claim 1, wherein said converting step is accomplished by use of a look-up table for rapid conversion of X and Y pixel addresses to an angle and a radius.

3. A method for processing a signal as in claim 2, wherein said look-up table is loaded during initialization of system.

4. A method for processing a signal that includes X, Y, and intensity data sets for each pixel of said sensor from an image sensor receiving a substantially ring shaped image as in claim 3, comprising the further step of discarding all data sets whose intensity signal does not exceed a predetermined value.

5. A method for processing a signal that includes X, Y, and intensity data sets for each pixel of said sensor from an image sensor receiving a substantially ring shaped image as in claim 4, wherein said predetermined value is set during calibration to include a range of values within an expected deviation of the radius of a tube being analyzed.

6. A method for processing a signal that includes X, Y, and intensity data sets for each pixel of said sensor from an image sensor receiving a substantially ring shaped image as in claim 4, wherein said predetermined value is set during calibration to include only a range of values within an expected deviation of the intensity of a reflected signal.

7. A method for processing a signal that includes X, Y, and intensity data sets for each pixel of said sensor from an image sensor receiving a substantially ring shaped image as in claim 4, further comprising the step of converting the analog output of an image sensor into a digital signal by synchronizing the clock of the image sensor with the intensity output to produce a X and a Y signal.

8. A method for processing a signal that includes X, Y, and intensity data sets for each pixel of said sensor from an image sensor receiving a substantially ring shaped image as in claim 4, further comprising the step of storing at least one of each angle, radius, intensity and data set in a register for one of downloading and processing.

9. A method of processing a signal that includes X, Y, and intensity data sets for each pixel of said image sensor receiving a substantially ring shaped image as in claim 8, further including the step of storing in said register at least one of each angle, radius, intensity and data set which falls within a preselected range.

* * * * *